United States Patent
Willer et al.

(10) Patent No.: US 8,030,440 B1
(45) Date of Patent: Oct. 4, 2011

(54) SYNTHESIS OF POLY-(3-NITRATOOXETANE)

(75) Inventors: Rodney L. Willer, Pass Christian, MS (US); Kurt Baum, Pasadena, CA (US); Wen-Huey Lin, Laguna Niguel, CA (US)

(73) Assignee: Fluorochem, Inc., Azusa, CA (US)

( * ) Notice: Subject to any disclaimer, the term of this patent is extended or adjusted under 35 U.S.C. 154(b) by 0 days.

(21) Appl. No.: 12/795,435

(22) Filed: Jun. 7, 2010

Related U.S. Application Data

(60) Provisional application No. 61/347,075, filed on May 21, 2010.

(51) Int. Cl.
*C08G 65/22* (2006.01)
*C07D 305/08* (2006.01)
*C06B 25/00* (2006.01)

(52) U.S. Cl. .......... 528/417; 528/408; 549/510; 149/88

(58) Field of Classification Search .......... 528/408, 528/417; 549/419, 510; 149/88
See application file for complete search history.

(56) References Cited

U.S. PATENT DOCUMENTS

| | | | |
|---|---|---|---|
| 4,395,561 A | 7/1983 | Baum et al. | |
| 5,120,827 A | 6/1992 | Willer et al. | |
| 5,313,000 A * | 5/1994 | Stewart | 568/613 |
| 5,663,383 A | 9/1997 | Stutz et al. | |

OTHER PUBLICATIONS

Baum, K, et. al., "Synthesis of Electron-Deficient Oxetanes. 3-Azidooxetane, 3-Nitrooxetane, and 3,3-Dinitrooxetane", J. Org. Chem., 26:2953-2956 (1983).
Leeming, W.B.H., et. al., "An Investigation Into polyGLYN Cure Stability", International Annual Conference of ICT, 99, CA 125, pp. 99-1 to 99-5 (1996).
Mason, B., et. al., "Abstract: Thermal Decomposition Behavior of Poly(3-nitraooxetane)", American Physical Society, 16th APS Topical Conference on Shock Compression of Condensed Matter, Jun. 28-Jul. 3, 2009, SAO/NASA ADS Physics Abstract Services, adsabs.harvard.edu/abs/2009APS..SHK.F1089M, abstract #CKF.10 (Jun. 2009).
Provatas, A., "Energetic Polymers and Plasticisers for Explosive Formulations—A Review of Recent Advances", Weapons Systems Division, Aeronautical and Maritime Research Laboratory, Department of Defence DSTO, DSTO-TR-0966 (Apr. 2000).
Willer, R., et. al., "Poly(Glycidyl Nitrate) Revisited", Proceedings for the Joint International Symposium on Compatibility of Plastics and Other Materials with Explosives, Propellants, Pyrotechnics and Processing of Explosives, Propellants and Ingredients, American Defense Preparedness Association, pp. 258-269 (Oct. 1989).
Willer, R., "Calculation of the Density and Detonation Properties of C, H, N, O and F Compounds: Use in the Design and Synthesis of New Energetic Materials", J. Mex. Chem. Soc., 53(3):108-119 (2009).

* cited by examiner

*Primary Examiner* — Fred M Teskin
(74) *Attorney, Agent, or Firm* — Joseph E. Mueth

(57) ABSTRACT

3-nitratooxetane.
Poly-(3-nitratooxetane).
The method of synthesizing 3-nitratooxetane comprising reacting 3-hydroxyoxetane with a nitration agent.
The method of synthesizing poly-(3-nitratooxetane) by polymerizing 3-nitratooxetane using a polyol initiator.

9 Claims, No Drawings

SYNTHESIS OF POLY-(3-NITRATOOXETANE)

Applicants claim the benefit of U.S. Provisional Patent Application 61/347,075, filed May 21, 2010.

BACKGROUND OF THE INVENTION

Hydroxy-terminated polybutadiene is widely used as a binder for polyurethane-based solid propellants because of its low viscosity and good low-temperature properties. The main chain in the isocyanate cured hydroxy-terminated polybutadiene is hydrocarbon. Binders with energetic groups on the chain are desirable for increased performance.

One of the most attractive examples on the basis of energy that has been studied is poly(glycidyl nitrate).

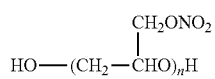
PGN

R. L. Willer and R. S. Day, *Proceedings of the APDA Joint International Symposium on the Compatibility of Plastics and Other Materials with Explosives, Propellants and Ingredients*, American Defense Preparedness Association, October, 1989, 258, Poly(Glycidyl Nitrate) Revisited; R. L. Willer, A. G. Stern, D. K. McGrath, 1990 *JANNAF Propulsion Meeting*, CPIA Publication 550, 3, 223, Poly(Glycidyl Nitrate) and Poly(Glycidyl Nitrate) Propellants. Unfortunately, isocyanate-cured PGN binders exhibits a cure reversion on aging, W. B. H. Leeming, E. J. Marshall, H. Bull, M. J. Rodgers, and N. C. Paul, *Int. Ann. Conference of ICT*, 99, 1-99 (1996) (CA 125:225892), that has limited its usefulness. The cure reversion has been ascribed to interaction of urethane nitrogens with hydrogens adjacent to the nitrate groups.

SUMMARY OF INVENTION

Briefly, the present invention comprises two novel compounds:

(1) 3-nitratooxetane, and
(2) poly-(3-nitratooxetane).

Still further, the invention comprises the method of synthesizing 3-nitratooxetane comprising reacting 3-hydroxyoxetane with a nitration agent, preferably concentrated nitric acid in a solution of acetic anhydride, and recovering 3-nitratooxetane.

This invention further comprises the method of synthesizing poly-(3-nitratooxetane) comprising polymerizing 3-nitratooxetane in the presence of a polyol, typically a diol or triol, and preferably 1,4-butanediol, as an initiator.

DESCRIPTION OF PREFERRED EMBODIMENTS

The synthesis of 3-hydroxyoxetane has been reported by a 4-step process. Acetic acid is added to epichlorohydrin, and the hydroxyl of the product is blocked with ethyl vinyl ether. Aqueous base hydrolyzes the acetate and closes the oxetane ring in one step. Removing the blocking group with acid gives 3-hydroxyoxetane. K. Baum, P. T. Berkowitz, V. Grakauskas, and T. G. Archibald, J. Org. Chem., 26:2953 (1983); and K. Baum, V. Grakauskas and P. T. Berkowitz, U.S. Pat. No. 4,395,561 (1983). Variations on this method using larger carboxylic acids instead of acetic acid have also been reported. W. Stutz, R. Waditschatka, K. Winter, M. von Frieling, R. Gressly, B. Jau, and S. Bürki, U.S. Pat. No. 5,663,383 (1997).

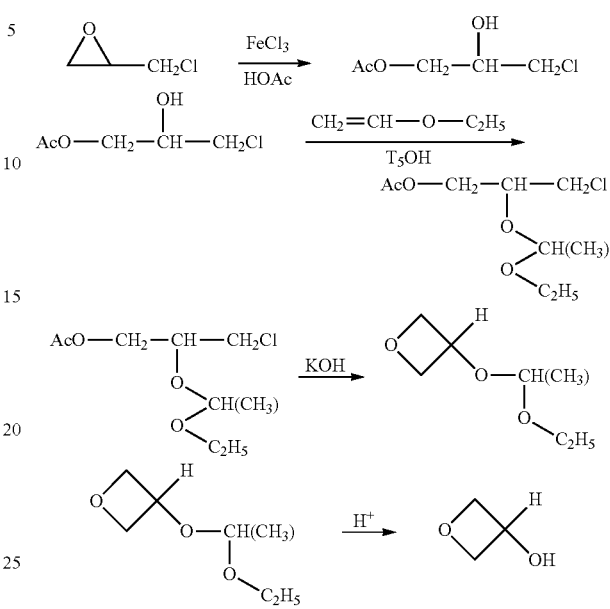

The present invention relates to the synthesis of poly-(3-nitratooxetane), PNO, which is isomeric with PGN. PNO has the formula:

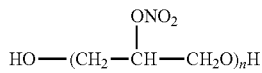

wherein n is an integer of from about 10 to about 10,000. Preferably, the molecular weight is from about 10,000 to 50,000.

PNO was prepared by the nitration of 3-hydroxyoxetane using a nitration agent, preferably nitric acid in acetic anhydride, to yield 3-nitratooxetane. The 3-nitratooxetane is then polymerized in the presence of a polyol initiator to yield PNO. The polyol initiator is typically a diol, or trial. The preferred initiator is 1,4-butanediol.

The nitration reaction was complete in 1 hour at 0-5° C., and the product was isolated by aqueous work-up. Other nitration agents can be similarly used. For example, trifluoroacetyl nitrate or nitrogen pentoxide in halogenated solvents, would be suitable in lieu of nitric acid in acetic anhydride. Typically, the nitration reaction is carried out at a temperature of from about minus 20° C. to about plus 20° C.

In polymerization, best results are obtained when $BF_3$ etherate or $BF_3$ tetrahydrofuran complex are first contacted with the polyol. After about 0.2 to about 3.0 hours, the $BF_3$ etherate or $BF_3$ tetrahydrofuran complex are vacuumed to remove evolved ether or tetrahydrofuran. The 3-nitratooxetane is then added along with an organic solvent such as halohydrocarbon, preferably, methylene chloride. The solution is stirred at or around room temperature until the PNO has formed. The PNO is then recovered.

Example 1

Synthesis of 3-nitratooxetane

A nitrating mixture was prepared by adding 100% nitric acid (13 g, 210 mmol) to a solution of acetic anhydride (20 g, 200 mmol) in anhydrous methylene chloride (15 ml) at 0-5° C. over a period of 5 min with stirring. The solution was stirred for one hour at 0-5° C., and a solution of 3-hydroxyoxetane (10 g, 135 mmol) in methylene chloride (10 ml) was added over 5 min. The solution was stirred at 5° C. for one hour. The solution was poured onto 20 ml of ice and the mixture was stirred until the ice melted. The organic layer was separated and washed with water (10 ml), saturated sodium bicarbonate (4×10 ml), and again with water (10 ml), and was dried over magnesium sulfate. Solvent was removed under vacuum, and distillation using a 3 inch Vigreux column gave 8.8 g (55% yield) of 3-nitratooxetane, by 55-57° C. at 10 mm Hg. H NMR (CDCl$_3$): 5.69 (1H, p), 4.95 (1H, d), 4.92 (1H, d), 4.70 (1H, d), 4.67 (1H, d) ppm. IR (neat): 2959 (m), 2888 (m), 1643 (s, —NO$_2$), 1478 (vw), 1459 (vw), 1373 (w), 1327 (s), 1281 (s), 1176 (m), 1115 (w), 1072 (s), 1041 (w), 978 (s), 928 (w), 885 (s), 855 (s), 755 (m), 692 (m) cm$^{-1}$. Mass spectrum: 120.02913; therefor [M H]$^+$ 120.02954.

Example 2

Synthesis of poly-(3-nitratooxetane)

1,4-Butanediol (0.133 g, 1.48 mmol) and BF$_3$ etherate (0.207 g, 1.46 mmol) were weighed in a 1-neck 50 ml round bottom flask. After stirring for 1 hour under nitrogen, the ether was removed by pumping at room temperature for 2 hours. Anhydrous methylene chloride (4 ml) was added to the mixture followed by the addition of 3-nitratooxetane (5.3 g, 44.5 mmol) in anhydrous methylene chloride (6 ml) over a period of 25 min. The solution was stirred at 25° C. for 16 hours. Additional methylene chloride (20 ml) was added. The solution was washed with saturated sodium bicarbonate solution (20 ml), water, and dried over anhydrous magnesium sulfate. Solvent was removed by rotary evaporation, followed by pumping at 35-40° C. for 5 hours to give 4.0 g (74% yield) of poly-(3-nitratooxetane), a is viscous light-yellow oil. Anal. Calcd. for C$_3$H$_5$NO$_4$: C, 30.30; H, 4.20; N, 11.80. Found: C, 30.53; H, 4.31; N, 11.89.

The following is a list of relevant properties for the poly-3-(nitratooxetane) (PNO).

Density($g/cc$)=1.44(averaged over several batches; range 1.42-1.45).

Impact 10/10 NF@200 cm (single batch, molecular weight 25,000, some variability in this number depending on batch but generally nothing fires below 95 cm). The impact test was carried out by placing a metal cup containing PNO on a metal anvil. A 1 kg weight is dropped onto the anvil from increasing heights until the PNO goes off, in this case, at a height of about 95 cm. By contrast, RDX goes off at about 25 cm.

Friction 10/10 NF@ 1000 lbs (single batch, molecular weight 25,000. The vast majority of batches have no registered sensitivity but very rarely we have irregular go's in friction sensitivity test. In the friction test, PNO is applied between two metal plates, weight is applied on the top of the upper plate and the upper plate is pulled laterally to create rubbing friction.

Electrostatic 10/10 NF@0.25 J (single batch, molecular weight 25,000, no variation across batches). In the electrostatic test, the PNO is hit with an electric spark to measure reproducibility of the PNO synthesis. The test showed little or no batch to batch variation.

DSC 177/202 (single batch, molecular weight 25,000, some variation across batches but onset and peak only shift by a few degrees). The differential scanning calorimetry (DSC) test involves putting the PNO in a cup and heating it. A temperature sensors detects the onset of an exotherm, indicating that decomposition has begun.

VTS (cc/g)=0.85 (single batch, molecular weight 25000, some variation across batches but always <2 cc/g). The VTS test also provides a measure of the batch-to-batch consistency of decomposition and stability. The PNO was maintained at elevated temperature and the volume of gas evolved from the PNO sample was measured.

Heat of formation data: based on formula; did not perform mass spectrometry measurement so the heat of formation is approximate.

TABLE 1

| Sample | $\Delta_c H°$ Cal/g | $\Delta_c H°$ kJ/g | $\Delta_f H°$ kJ/g |
|---|---|---|---|
| PNO 1 | −3201.70 ± 25.29 | −13.41 ± 0.11 | −2.53 ± 0.10 |
| PNO 2 | −3308.70 ± 15 | −13.84 ± 0.06 | −2.04 |
| PGN Lot E-15 | −3233.20 ± 11 | −13.53 ± 0.05 | −2.42 |

$\Delta_f H°$ is obtained with the equation:

$$\Delta_f H°(\text{polymer})=3\Delta_f H°(CO_2)+5/2\Delta_f H°(H_2O)-\Delta_c H°(\text{polymer})$$

where $\Delta_f H°$ (CO$_2$)=−393.5 kJ/mol and $\Delta_f H°$ (H$_2$O)=−285.8 kJ/mol.

Liquid Drop weight test. The following results show the results comparing PNO with N-propyl nitrate and isopropyl nitrate.

PNO: $E_{50}$:173 kg cm (low fire 164 kg cm)
N-propyl nitrate: $E_{50}$:29 kg cm (low fire 28 kg cm)
Isopropyl nitrate: $E_{50}$:30 kg cm (low fire 28 kg cm)

TABLE 2

The comparative properties of PNO and PGN are shown in the following table:

| | PNO | PGN |
|---|---|---|
| Impact sensitivity | 89 cm (50%) | 110 cm (50%) |
| | 63 cm (low fire) | 100 cm (low fire) |
| Friction | 10/10 no fire | 10/10 no fire |
| | @ 1000 lbs | @ 398 lbs |
| ESD | 10/10 no fire | 10/10 no fire |
| | @ 0.25 joules | @ 0.25 joules |
| VTS | 1.6 cc/g @ 80° C. | 0.1 cc/g @ 80° C. |
| | (no stabilizer) | (With stabilizer) |
| DSC | Onset 180° C. | Onset 164-194° C. |
| | Max 210° C. | Max 215° C. |

Gumstocks were prepared by reacting PGN and PNU with the same organic polyisocyanate and the two resulting polyurethanes observed for two months. The poly(glycidyl nitrate) samples showed depolymerization while the poly-(3-nitratooxetane) samples showed no changes at all.

The superior long term stability of the PNO based gumstock is important in applications where high energy binders are required such as in explosives and rocket propellants.

The invention claimed is:
1. 3-nitratooxetane.
2. Poly-(3-nitratooxetane).
3. The compound of claim 2 having a molecular weight of from 10,000 to 50,000.
4. The compound of claim 2 having a molecular weight is of about 25,000.

5. The method of synthesizing 3-nitratooxetane comprising reacting 3-hydroxyoxetane with a nitration agent and recovering 3-nitratooxetane.

6. The method of claim 5 wherein the nitration agent is concentrated nitric acid in a solution of acetic anhydride.

7. The method of synthesizing poly-(3-nitratooxetane) comprising polymerizing 3-nitratooxetane in the presence of a polyol initiator.

8. The method of claim 7 wherein the polyol is 1,4 butanediol.

9. The method of claim 7 wherein $BF_3$ etherate or $BF_3$ tetrahydrofuran complex is combined with the polyol and any gaseous evolution products are removed prior to addition of 3-nitratooxetane.

* * * * *